(12) United States Patent
Rashbaum et al.

(10) Patent No.: US 9,597,194 B2
(45) Date of Patent: Mar. 21, 2017

(54) INTERVERTEBRAL DISC PROSTHESIS

(71) Applicant: LDR Medical, Rosières Près Troyes (FR)

(72) Inventors: Ralph Rashbaum, Plano, TX (US); Kee D. Kim, Davis, CA (US); Hyun Bae, Santa Monica, CA (US)

(73) Assignee: LDR Medical, Sainte-Savine (FR)

( * ) Notice: Subject to any disclaimer, the term of this patent is extended or adjusted under 35 U.S.C. 154(b) by 0 days.

(21) Appl. No.: 14/659,587

(22) Filed: Mar. 16, 2015

(65) Prior Publication Data

US 2015/0190240 A1 Jul. 9, 2015

Related U.S. Application Data

(63) Continuation of application No. 12/955,898, filed on Nov. 29, 2010, now Pat. No. 8,979,932, which is a (Continued)

(30) Foreign Application Priority Data

Sep. 23, 2005 (FR) ..................... 05 09740

(51) Int. Cl.
*A61F 2/44* (2006.01)
*A61B 17/064* (2006.01)
*A61F 2/30* (2006.01)

(52) U.S. Cl.
CPC ........ *A61F 2/4425* (2013.01); *A61F 2/30749* (2013.01); *A61B 17/0642* (2013.01); (Continued)

(58) Field of Classification Search
CPC .. A61B 17/064; A61B 17/0642; A61F 2/4425
See application file for complete search history.

(56) References Cited

U.S. PATENT DOCUMENTS

| 344,683 A | 6/1886 | Sherer |
|---|---|---|
| 1,025,596 A | 5/1912 | Strawser |

(Continued)

FOREIGN PATENT DOCUMENTS

| DE | 3741493 | 6/1989 |
|---|---|---|
| DE | 4327054 | 4/1995 |

(Continued)

OTHER PUBLICATIONS

U.S. Patent & Trademark Office; Office Action in U.S. Appl. No. 12/884,664; Sep. 26, 2012; USPTO; Alexandria, Virgina; All Pages.

(Continued)

*Primary Examiner* — Ellen C Hammond
(74) *Attorney, Agent, or Firm* — Lauff Law PLLC

(57) ABSTRACT

Anchors for retaining an intervertebral device used for spinal treatment are disclosed. In one embodiment, the anchor has a plate-like body extending between the ends of the anchor. In another embodiment, the anchor has a bar-shaped body that is disposed along the top or bottom of the intervertebral device when the anchor is deployed. Various latches, retainers, and locking structures for holding the intervertebral device and the anchor together are disclosed.

12 Claims, 4 Drawing Sheets

Related U.S. Application Data continuation of application No. 11/341,007, filed on Jan. 27, 2006, now Pat. No. 7,842,088.

(52) U.S. Cl.
CPC ... *A61B 2017/0647* (2013.01); *A61F 2/30734* (2013.01); *A61F 2002/305* (2013.01); *A61F 2002/30331* (2013.01); *A61F 2002/30365* (2013.01); *A61F 2002/30369* (2013.01); *A61F 2002/30576* (2013.01); *A61F 2002/30616* (2013.01); *A61F 2002/30662* (2013.01); *A61F 2002/30878* (2013.01); *A61F 2002/30884* (2013.01); *A61F 2002/30904* (2013.01); *A61F 2002/443* (2013.01); *A61F 2220/0016* (2013.01); *A61F 2220/0025* (2013.01); *A61F 2220/0033* (2013.01)

(56) References Cited

U.S. PATENT DOCUMENTS

| | | | |
|---|---|---|---|
| 1,121,484 | A | 12/1914 | Crites |
| 3,875,595 | A | 4/1975 | Froning |
| 3,948,262 | A | 4/1976 | Zaffaroni |
| 4,507,115 | A | 3/1985 | Kambara et al. |
| 4,599,086 | A | 7/1986 | Doty |
| 4,834,757 | A | 5/1989 | Brantigan |
| 4,904,261 | A | 2/1990 | Dove et al. |
| 5,306,307 | A | 4/1994 | Senter et al. |
| 5,326,205 | A | 7/1994 | Anspach, Jr. et al. |
| 5,425,772 | A | 6/1995 | Brantigan |
| 5,452,499 | A * | 9/1995 | Schmidt et al. ............... 24/453 |
| 5,458,638 | A | 10/1995 | Kuslich et al. |
| 5,501,695 | A | 3/1996 | Anspach, Jr. et al. |
| 5,658,335 | A | 8/1997 | Allen |
| 5,683,394 | A | 11/1997 | Rinner |
| 5,713,899 | A | 2/1998 | Marnay et al. |
| 5,755,798 | A | 5/1998 | Papavero et al. |
| 5,782,830 | A | 7/1998 | Farris |
| 5,810,820 | A | 9/1998 | Santori et al. |
| 5,849,004 | A | 12/1998 | Bramlet |
| 5,860,973 | A | 1/1999 | Michelson |
| 5,865,845 | A | 2/1999 | Thalgott |
| 5,888,222 | A | 3/1999 | Coates et al. |
| 5,888,223 | A | 3/1999 | Bray, Jr. |
| 5,888,227 | A | 3/1999 | Cottle |
| 5,888,228 | A | 3/1999 | Knothe et al. |
| 5,976,139 | A | 11/1999 | Bramlet |
| 5,989,289 | A | 11/1999 | Coates et al. |
| 6,045,579 | A | 4/2000 | Hochshuler et al. |
| 6,059,787 | A | 5/2000 | Allen |
| 6,066,174 | A | 5/2000 | Farris |
| 6,080,193 | A | 6/2000 | Hochshuler et al. |
| 6,111,164 | A | 8/2000 | Rainey et al. |
| 6,120,502 | A | 9/2000 | Michelson |
| 6,123,705 | A | 9/2000 | Michelson |
| 6,143,032 | A | 11/2000 | Schafer et al. |
| 6,174,311 | B1 | 1/2001 | Branch et al. |
| 6,179,875 | B1 | 1/2001 | Von Strempel |
| 6,183,474 | B1 | 2/2001 | Bramlet et al. |
| 6,206,923 | B1 | 3/2001 | Boyd et al. |
| 6,210,442 | B1 | 4/2001 | Wing et al. |
| 6,231,610 | B1 | 5/2001 | Geisler |
| 6,235,059 | B1 | 5/2001 | Benezech et al. |
| 6,241,733 | B1 | 6/2001 | Nicholson et al. |
| 6,241,770 | B1 | 6/2001 | Michelson |
| 6,245,108 | B1 | 6/2001 | Biscup |
| 6,251,140 | B1 | 6/2001 | Marino et al. |
| 6,258,089 | B1 | 7/2001 | Campbell et al. |
| 6,258,125 | B1 | 7/2001 | Paul et al. |
| 6,261,295 | B1 | 7/2001 | Nicholson et al. |
| 6,267,764 | B1 | 7/2001 | Elberg |
| 6,348,071 | B1 | 2/2002 | Steffee et al. |
| 6,350,283 | B1 | 2/2002 | Michelson |
| 6,383,186 | B1 | 5/2002 | Michelson |
| 6,395,031 | B1 | 5/2002 | Foley et al. |
| 6,432,106 | B1 | 8/2002 | Fraser |
| 6,432,107 | B1 | 8/2002 | Ferree |
| 6,454,769 | B2 | 9/2002 | Wagner et al. |
| 6,458,159 | B1 | 10/2002 | Thalgott |
| 6,461,359 | B1 | 10/2002 | Tribus et al. |
| 6,482,233 | B1 | 11/2002 | Aebi et al. |
| 6,482,584 | B1 | 11/2002 | Mills et al. |
| 6,497,726 | B1 | 12/2002 | Carter et al. |
| 6,527,803 | B1 | 3/2003 | Crozet et al. |
| 6,554,863 | B2 | 4/2003 | Paul et al. |
| 6,576,016 | B1 | 6/2003 | Hochshuler et al. |
| 6,599,294 | B2 | 7/2003 | Fuss et al. |
| 6,605,089 | B1 | 8/2003 | Michelson |
| 6,610,065 | B1 | 8/2003 | Branch et al. |
| 6,613,278 | B1 | 9/2003 | Mills et al. |
| 6,620,163 | B1 | 9/2003 | Michelson |
| 6,635,086 | B2 | 10/2003 | Lin |
| 6,635,087 | B2 | 10/2003 | Angelucci et al. |
| 6,652,584 | B2 | 11/2003 | Michelson |
| 6,652,818 | B1 | 11/2003 | Mills et al. |
| 6,660,038 | B2 | 12/2003 | Boyer, II et al. |
| 6,666,890 | B2 | 12/2003 | Michelson |
| 6,676,703 | B2 | 1/2004 | Biscup |
| 6,695,846 | B2 | 2/2004 | Richelsoph et al. |
| 6,706,067 | B2 | 3/2004 | Shimp et al. |
| 6,712,818 | B1 | 3/2004 | Michelson |
| 6,733,531 | B1 | 5/2004 | Trieu |
| 6,743,255 | B2 | 6/2004 | Ferree |
| 6,743,256 | B2 | 6/2004 | Mason |
| 6,743,257 | B2 | 6/2004 | Castro |
| 6,758,849 | B1 | 7/2004 | Michelson |
| RE38,614 | E | 10/2004 | Paul et al. |
| 6,800,092 | B1 | 10/2004 | Williams et al. |
| 6,805,713 | B1 | 10/2004 | Carter et al. |
| 6,964,687 | B1 | 11/2005 | Bernard et al. |
| 7,018,412 | B2 | 3/2006 | Ferreira et al. |
| 7,048,762 | B1 | 5/2006 | Sander et al. |
| 7,048,765 | B1 | 5/2006 | Grooms et al. |
| 7,051,610 | B2 | 5/2006 | Stoianovici et al. |
| 7,137,984 | B2 | 11/2006 | Michelson |
| 7,235,082 | B2 | 6/2007 | Bartish et al. |
| 7,255,698 | B2 | 8/2007 | Michelson |
| 7,276,081 | B1 | 10/2007 | Coates et al. |
| 7,303,583 | B1 | 12/2007 | Schar et al. |
| 7,361,196 | B2 | 4/2008 | Fallin et al. |
| 7,404,795 | B2 | 7/2008 | Ralph et al. |
| 7,455,684 | B2 | 11/2008 | Gradel et al. |
| 7,473,276 | B2 | 1/2009 | Aebi et al. |
| 7,479,160 | B2 | 1/2009 | Branch et al. |
| 7,563,284 | B2 | 7/2009 | Coppes et al. |
| 7,563,286 | B2 | 7/2009 | Gerber et al. |
| 7,604,654 | B2 | 10/2009 | Fallin et al. |
| 7,611,538 | B2 * | 11/2009 | Belliard ............... A61F 2/4425 623/17.15 |
| 7,625,393 | B2 | 12/2009 | Fallin et al. |
| 7,637,953 | B2 | 12/2009 | Branch et al. |
| 7,695,516 | B2 * | 4/2010 | Zeegers .................... 623/17.14 |
| 7,744,602 | B2 | 6/2010 | Teeny et al. |
| 7,771,478 | B2 * | 8/2010 | Navarro et al. ............ 623/17.15 |
| 7,842,088 | B2 * | 11/2010 | Rashbaum et al. ........ 623/17.15 |
| 7,846,188 | B2 | 12/2010 | Moskowitz et al. |
| 7,905,886 | B1 | 3/2011 | Curran et al. |
| 8,080,062 | B2 | 12/2011 | Armstrong et al. |
| 8,097,034 | B2 | 1/2012 | Michelson |
| 8,118,873 | B2 | 2/2012 | Humphreys et al. |
| 8,137,405 | B2 | 3/2012 | Kostuik et al. |
| 8,147,556 | B2 | 4/2012 | Louis et al. |
| 8,167,946 | B2 | 5/2012 | Michelson |
| 8,167,949 | B2 | 5/2012 | Tyber et al. |
| 8,167,950 | B2 | 5/2012 | Aferzon et al. |
| 8,182,539 | B2 | 5/2012 | Tyber et al. |
| 8,187,329 | B2 | 5/2012 | Theofilos |
| 8,187,332 | B2 | 5/2012 | McLuen |
| 8,216,312 | B2 | 7/2012 | Gray |
| 8,241,359 | B2 | 8/2012 | Davis et al. |
| 8,257,443 | B2 | 9/2012 | Kamran et al. |
| 8,303,663 | B2 | 11/2012 | Jimenez et al. |
| 8,313,528 | B1 | 11/2012 | Wensel |

(56) References Cited

U.S. PATENT DOCUMENTS

| | | |
|---|---|---|
| 8,323,345 B2 | 12/2012 | Sledge |
| 8,343,197 B2 | 1/2013 | Gonzalez-Hernandez |
| 8,349,015 B2 | 1/2013 | Bae et al. |
| 8,353,219 B2 | 1/2013 | Brackett et al. |
| 8,465,546 B2 | 6/2013 | Jodaitis et al. |
| 8,535,352 B2 | 9/2013 | Altarac et al. |
| 8,545,563 B2 | 10/2013 | Brun et al. |
| 8,617,245 B2 | 12/2013 | Brett |
| 8,685,100 B2 | 4/2014 | Jodaitis et al. |
| 8,696,681 B2 | 4/2014 | Harris et al. |
| 8,753,397 B2 | 6/2014 | Beaurain et al. |
| 8,771,284 B2 | 7/2014 | Rashbaum et al. |
| 8,858,635 B2 | 10/2014 | Hovorka et al. |
| 8,974,532 B2 | 3/2015 | Zeegers |
| 8,979,932 B2 * | 3/2015 | Rashbaum et al. ........ 623/17.14 |
| 9,044,337 B2 | 6/2015 | Dinville et al. |
| 2001/0018614 A1 | 8/2001 | Bianchi |
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0059938 A1 | 5/2002 | Fogarty et al. |
| 2002/0070565 A1 * | 6/2002 | Szapucki et al. ............. 292/228 |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0087212 A1 | 7/2002 | James et al. |
| 2002/0106393 A1 | 8/2002 | Bianchi et al. |
| 2002/0107572 A1 | 8/2002 | Foley et al. |
| 2002/0119437 A1 | 8/2002 | Grooms et al. |
| 2002/0138143 A1 | 9/2002 | Grooms et al. |
| 2002/0151893 A1 | 10/2002 | Santilli |
| 2002/0161375 A1 | 10/2002 | Ralph et al. |
| 2002/0165612 A1 | 11/2002 | Gerber et al. |
| 2003/0023304 A1 | 1/2003 | Carter et al. |
| 2003/0027125 A1 | 2/2003 | Mills et al. |
| 2003/0060886 A1 | 3/2003 | Van Hoeck et al. |
| 2003/0069640 A1 | 4/2003 | Ferreira et al. |
| 2003/0097179 A1 | 5/2003 | Carter et al. |
| 2003/0100950 A1 | 5/2003 | Moret |
| 2003/0139815 A1 | 7/2003 | Grooms et al. |
| 2003/0149484 A1 | 8/2003 | Michelson |
| 2003/0167091 A1 | 9/2003 | Scharf |
| 2003/0191531 A1 | 10/2003 | Berry et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0233147 A1 | 12/2003 | Nicholson et al. |
| 2004/0073307 A1 | 4/2004 | Keller |
| 2004/0073313 A1 | 4/2004 | Link et al. |
| 2004/0097929 A1 | 5/2004 | Branch et al. |
| 2004/0115172 A1 | 6/2004 | Bianchi et al. |
| 2004/0127990 A1 | 7/2004 | Bartish, Jr. et al. |
| 2004/0127993 A1 | 7/2004 | Kast et al. |
| 2004/0127994 A1 | 7/2004 | Kast et al. |
| 2004/0172130 A1 | 9/2004 | Nakahara et al. |
| 2004/0210308 A1 | 10/2004 | Carter et al. |
| 2004/0230306 A1 | 11/2004 | Hoeck et al. |
| 2005/0004672 A1 | 1/2005 | Pafford et al. |
| 2005/0027360 A1 | 2/2005 | Webb et al. |
| 2005/0027362 A1 | 2/2005 | Williams et al. |
| 2005/0038511 A1 | 2/2005 | Martz et al. |
| 2005/0065611 A1 * | 3/2005 | Huppert et al. ........... 623/17.15 |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0119744 A1 | 6/2005 | Buskirk et al. |
| 2005/0119747 A1 | 6/2005 | Fabris Monterumici et al. |
| 2005/0125029 A1 | 6/2005 | Bernard et al. |
| 2005/0165483 A1 | 7/2005 | Ray, III et al. |
| 2005/0171554 A1 | 8/2005 | Estes et al. |
| 2005/0283236 A1 | 12/2005 | Razian |
| 2005/0288788 A1 | 12/2005 | Dougherty-Shah |
| 2006/0085071 A1 | 4/2006 | Lechmann et al. |
| 2006/0121084 A1 | 6/2006 | Borden et al. |
| 2006/0136063 A1 * | 6/2006 | Zeegers ..................... 623/17.14 |
| 2006/0178745 A1 * | 8/2006 | Bartish, Jr. ............. A61F 2/442 |
| | | 623/17.13 |
| 2006/0235426 A1 | 10/2006 | Lim et al. |
| 2006/0241621 A1 | 10/2006 | Moskowitz et al. |
| 2006/0241761 A1 | 10/2006 | Gately |
| 2006/0276899 A1 | 12/2006 | Zipnick et al. |
| 2007/0049943 A1 | 3/2007 | Moskowitz et al. |
| 2007/0093850 A1 | 4/2007 | Harris et al. |
| 2007/0106388 A1 | 5/2007 | Michelson |
| 2007/0142843 A1 | 6/2007 | Dye |
| 2007/0162128 A1 | 7/2007 | DeRidder et al. |
| 2007/0168040 A1 | 7/2007 | Raymond |
| 2007/0208345 A1 | 9/2007 | Marnay et al. |
| 2007/0270960 A1 | 11/2007 | Bonin et al. |
| 2007/0293948 A1 | 12/2007 | Bagga et al. |
| 2008/0021562 A1 | 1/2008 | Huppert |
| 2008/0033432 A1 | 2/2008 | McGraw et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0132949 A1 | 6/2008 | Aferzon et al. |
| 2008/0161933 A1 | 7/2008 | Grotz et al. |
| 2008/0177306 A1 | 7/2008 | Lamborne et al. |
| 2009/0005874 A1 | 1/2009 | Fleischmann et al. |
| 2009/0112271 A1 | 4/2009 | Moskowitz et al. |
| 2009/0186333 A1 | 7/2009 | Mills et al. |
| 2009/0216331 A1 | 8/2009 | Grotz et al. |
| 2009/0222092 A1 | 9/2009 | Davis et al. |
| 2009/0270990 A1 | 10/2009 | Louis et al. |
| 2010/0016903 A1 | 1/2010 | Matityahu et al. |
| 2010/0016974 A1 | 1/2010 | Janowski et al. |
| 2010/0050276 A1 | 2/2010 | DePaepe |
| 2010/0057207 A1 | 3/2010 | Ray, III et al. |
| 2010/0063554 A1 | 3/2010 | Branch et al. |
| 2010/0070046 A1 | 3/2010 | Steinberg |
| 2010/0082104 A1 | 4/2010 | Carter et al. |
| 2010/0217396 A1 | 8/2010 | Bianchi et al. |
| 2010/0268349 A1 | 10/2010 | Bianchi et al. |
| 2010/0298941 A1 | 11/2010 | Hes et al. |
| 2011/0112587 A1 | 5/2011 | Patel et al. |
| 2011/0178599 A1 | 7/2011 | Brett |
| 2011/0301707 A1 | 12/2011 | Buskirk et al. |
| 2012/0004660 A1 | 1/2012 | Grooms et al. |
| 2012/0022654 A1 | 1/2012 | Farris et al. |
| 2012/0078371 A1 | 3/2012 | Gamache et al. |
| 2012/0116466 A1 | 5/2012 | Dinville et al. |
| 2012/0191196 A1 | 7/2012 | Louis et al. |
| 2012/0197404 A1 | 8/2012 | Brun et al. |
| 2012/0330424 A1 | 12/2012 | Zeegers |
| 2013/0013006 A1 | 1/2013 | Rashbaum et al. |
| 2013/0150968 A1 | 6/2013 | Dinville et al. |
| 2013/0166029 A1 | 6/2013 | Dinville et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0114413 A1 | 4/2014 | Allain et al. |
| 2015/0051702 A1 | 2/2015 | Chataigner et al. |

FOREIGN PATENT DOCUMENTS

| | | |
|---|---|---|
| EP | 0042271 | 12/1981 |
| EP | 0176728 | 4/1986 |
| EP | 0667127 | 8/1995 |
| EP | 0965313 | 12/1999 |
| EP | 2113228 | 11/2009 |
| EP | 2327375 | 6/2011 |
| EP | 2340788 | 7/2011 |
| EP | 2363080 | 9/2011 |
| FR | 2703580 | 10/1994 |
| FR | 2733413 | 10/1996 |
| FR | 2747034 | 10/1997 |
| FR | 2808995 | 11/2001 |
| FR | 2823095 | 10/2002 |
| FR | 2827156 | 1/2003 |
| FR | 2861582 | 5/2005 |

(56) References Cited

FOREIGN PATENT DOCUMENTS

| | | |
|---|---|---|
| FR | 2897259 | 8/2007 |
| FR | 2987256 | 8/2013 |
| FR | 3005569 | 11/2014 |
| FR | 3016793 | 7/2015 |
| RU | 2004218 | 12/1993 |
| WO | WO9508306 | 3/1995 |
| WO | WO9715248 | 5/1997 |
| WO | WO9801091 | 1/1998 |
| WO | WO9855052 | 12/1998 |
| WO | WO9963914 | 12/1999 |
| WO | WO0024327 | 5/2000 |
| WO | WO0170141 | 9/2001 |
| WO | WO0187194 | 11/2001 |
| WO | WO2004080356 | 9/2004 |
| WO | WO2006102269 | 9/2006 |
| WO | WO2007093900 | 8/2007 |
| WO | WO2008044057 | 4/2008 |
| WO | WO2010090801 | 8/2010 |
| WO | WO2011129973 | 10/2011 |
| WO | WO2014184367 | 11/2014 |
| WO | WO2015114122 | 8/2015 |

OTHER PUBLICATIONS

LDR Medical, by its attorneys; Reply to Office Action in U.S. Appl. No. 12/884,664; Oct. 16, 2012; USPTO; Alexandria, Virgina; All Pages.
U.S. Patent & Trademark Office; Examiner Interview Summary in U.S. Appl. No. 12/884,664; Dec. 18, 2012; USPTO; Alexandria, Virgina; All Pages.
U.S. Patent & Trademark Office; Office Action in U.S. Appl. No. 12/884,664; Jan. 15, 2013; USPTO; Alexandria, Virgina; All Pages.
LDR Medical, by its attorneys; Reply to Office Action in U.S. Appl. No. 12/884,664; Apr. 10, 2013; USPTO; Alexandria, Virgina; All Pages.
U.S. Patent & Trademark Office; Notice of Allowance in U.S. Appl. No. 12/884,664; Aug. 6, 2013; USPTO; Alexandria, Virgina; All Pages.
U.S. Patent & Trademark Office; Office Action in U.S. Appl. No. 14/064,434; Jan. 13, 2014; USPTO; Alexandria, Virgina; All Pages.
LDR Medical, by its attorneys; Reply to Office Action in U.S. Appl. No. 14/064,434; Apr. 14, 2014; USPTO; Alexandria, Virgina; All Pages.
U.S. Patent & Trademark Office; Office Action in U.S. Appl. No. 14/064,434; May 5, 2014; USPTO; Alexandria, Virgina; All Pages.
LDR Medical, by its attorneys; Reply to Office Action in U.S. Appl. No. 14/064,434; Aug. 27, 2014; USPTO; Alexandria, Virgina; All Pages.
U.S. Patent & Trademark Office; Notice of Allowance in U.S. Appl. No. 14/064,434; Sep. 8, 2014; USPTO; Alexandria, Virgina; All Pages.
U.S. Patent & Trademark Office; Office Action in U.S. Appl. No. 14/594,770; Jul. 1, 2015; USPTO; Alexandria, Virgina; All Pages.
LDR Medical, by its attorneys; Reply to Office Action in U.S. Appl. No. 14/064,434; Nov. 2, 2015; USPTO; Alexandria, Virgina; All Pages.
LDR Medical, by its attorneys; Reply to Office Action in U.S. Appl. No. 12/025,677; Aug. 19, 2014; USPTO, Alexandria, Virgina; All Pages.
U.S. Patent & Trademark Office; Office Action in U.S. Appl. No. 12/025,677; Nov. 7, 2014; USPTO; Alexandria, Virgina; All Pages.
LDR Medical, by its attorneys; Reply to Office Action in U.S. Appl. No. 12/025,677; May 6, 2015; USPTO; Alexandria, Virgina; All Pages.
U.S. Patent & Trademark Office; Office Action in U.S. Appl. No. 12/025,677; Aug. 12, 2015; USPTO; Alexandria, Virginia; All Pages.
LDR Medical, by its attorneys; Reply to Office Action in U.S. Appl. No. 12/025,677; Nov. 12, 2015; USPTO; Alexandria, Virgina; All Pages.
U.S. Patent & Trademark Office; Reply to Office Action in U.S. Appl. No. 13/616,448; Dec. 23, 2013; USPTO; Alexandria, Virgina; All Pages.
U.S. Patent & Trademark Office; Notice of Allowance in U.S. Appl. No. 13/616,448; Apr. 21, 2014; USPTO; Alexandria, Virginia; All Pages.
U.S. Patent & Trademark Office; Notice of allowance in U.S. Appl. No. 11/051,710; Jun. 11, 2014; USPTO; Alexandria, Virgina; All Pages.
LDR Medical, by its attorneys; Reply to Office Action in U.S. Appl. No. 13/215,123; May 19, 2014; USPTO; Alexandria, Virgina; All Pages.
U.S. Patent & Trademark Office; Notice of Allowance in U.S. Appl. No. 13/215,123; Aug. 29, 2014; USPTO; Alexandria, Virgina; All Pages.
U.S. Patent & Trademark Office; Notice of Allowance in U.S. Appl. No. 13/215,123; Jan. 20, 2015; USPTO; Alexandria, Virgina; All Pages.
U.S. Patent & Trademark Office; Office Action in U.S. Appl. No. 14/642,696; Sep. 2, 2015; USPTO; Alexandria, Virgina; All Pages.
LDR Medical, by its attorneys; Reply to Office Action in U.S. Appl. No. 14/642,696; Dec. 2, 2015; USPTO; Alexandria, Virgina; All Pages.
LDR Medical, by its attorneys; Reply to Office Action in U.S. Appl. No. 13/892,933; Apr. 2, 2014; USPTO; Alexandria, Virgina; All Pages.
U.S. Patent & Trademark Office; Office Action in U.S. Appl. No. 13/892,933; Jul. 28, 2014; USPTO; Alexandria, Virginia; All Pages.
LDR Medical, by its attorneys; Reply to Office Action in U.S. Appl. No. 13/892,933; Dec. 29, 2014; USPTO; Alexandria, Virgina; All Pages.
U.S. Patent & Trademark Office; Notice of Allowance in U.S. Appl. No. 13/892,933; Feb. 13, 2015; USPTO; Alexandria, Virginia; All Pages.
U.S. Patent & Trademark Office; Notice of Allowance in U.S. Appl. No. 13/892,933; Sep. 14, 2015; USPTO; Alexandria, Virgina; All Pages.
U.S. Patent & Trademark Office; Office Action in U.S. Appl. No. 12/955,898; Jun. 1, 2012; USPTO; Alexandria, Virgina; All Pages.
LDR Medical, by its attorneys; Reply to Office Action in U.S. Appl. No. 12/955,898; Dec. 3, 2012; USPTO; Alexandria, Virgina; All Pages.
U.S. Patent & Trademark Office; Office Action in U.S. Appl. No. 12/955,898; Jan. 10, 2013; USPTO; Alexandria, Virgina; All Pages.
LDR Medical, by its attorneys; Reply to Office Action in U.S. Appl. No. 12/955,898; Jul. 10, 2013; USPTO; Alexandria, Virgina; All Pages.
U.S. Patent & Trademark Office; Office Action in U.S. Appl. No. 12/955,898; Mar. 3, 2014; USPTO; Alexandria, Virgina; All Pages.
LDR Medical, by its attorneys; Reply to Office Action in U.S. Appl. No. 12/955,898; Aug. 4, 2014; USPTO; Alexandria, Virgina; All Pages.
U.S. Patent & Trademark Office; Notice of Allowance in U.S. Appl. No. 12/955,898; Aug. 8, 2014; USPTO; Alexandria, Virgina; All Pages.
U.S. Patent & Trademark Office; Notice of Allowance in U.S. Appl. No. 12/955,898; Jan. 29, 2015; USPTO; Alexandria, Virgina; All Pages.
U.S. Patent & Trademark Office; Office Action in U.S. Appl. No. 14/659,587; Apr. 16, 2015; USPTO; Alexandria, Virginia; All Pages.
LDR Medical, by its attorneys; Reply to Office Action in U.S. Appl. No. 14/659,587; Sep. 16, 2015; USPTO; Alexandria, Virginia; All Pages.
U.S. Patent & Trademark Office; Notice of Allowance in U.S. Appl. No. 14/659,587; Oct. 9, 2015; USPTO; Alexandria, Virginia; All Pages.
U.S. Patent & Trademark Office; Appeal Decision in U.S. Appl. No. 11/362,253; Jul. 17, 2015; USPTO; Alexandria, Virgina; All Pages.
U.S. Patent & Trademark Office; Appeal Decision in U.S. Appl. No. 11/362,253; Sep. 17, 2015; USPTO; Alexandria, Virginia; All Pages.

(56) References Cited

OTHER PUBLICATIONS

U.S. Patent & Trademark Office; Notice of Allowance in U.S. Appl. No. 11/362,253; Oct. 14, 2015; USPTO; Alexandria, Virgina; All Pages.
U.S. Patent & Trademark Office; Office Action in U.S. Appl. No. 14/325,317; Dec. 24, 2014; USPTO; Alexandria, Virgina; All Pages.
LDR Medical, by its attorneys; Reply to Office Action in U.S. Appl. No. 14/325,317; Mar. 24, 2015; USPTO; Alexandria, Virgina; All Pages.
U.S. Patent & Trademark Office; Notice of Allowance in U.S. Appl. No. 14/325,317; May 6, 2015; USPTO; Alexandria, Virgina; All Pages.
U.S. Patent & Trademark Office; Notice of Allowance in U.S. Appl. No. 12/025,677; Jan. 7, 2016; USPTO; Alexandria, Virgina; All Pages.
U.S. Patent & Trademark Office; Office Action in U.S. Appl. No. 14/726,557; Dec. 30, 2015; USPTO; Alexandria, Virgina; All Pages.
U.S. Patent & Trademark Office; Office Action in U.S. Appl. No. 13/919,704; Jun. 2, 2014; USPTO; Alexandria, Virgina; All Pages.
LDR Medical, by its attorneys; Reply to Office Action in U.S. Appl. No. 13/919,704; Dec. 2, 2014; USPTO; Alexandria, Virgina; All Pages.
U.S. Patent & Trademark Office; Office Action in U.S. Appl. No. 13/919,704; Mar. 13, 2015; USPTO; Alexandria, Virgina; All Pages.
LDR Medical, by its attorneys; Reply to Office Action in U.S. Appl. No. 13/919,704; Sep. 14, 2015; USPTO; Alexandria, Virgina; All Pages.
U.S. Patent & Trademark Office; Office Action in U.S. Appl. No. 14/242,177; Dec. 22, 2014; USPTO; Alexandria, Virgina; All Pages.
LDR Medical, by its attorneys; Reply to Office Action in U.S. Appl. No. 14/242,177; Jun. 22, 2015; USPTO; Alexandria, Virgina; All Pages.
U.S. Patent & Trademark Office; Office Action in U.S. Appl. No. 14/242,177; Oct. 15, 2015; USPTO; Alexandria, Virgina; All Pages.
U.S. Patent & Trademark Office; Office Action in U.S. Appl. No. 13/919,704; Dec. 29, 2015; USPTO; Alexandria, Virgina; All Pages.
LDR Medical, by its attorneys; Reply to Office Action in U.S. Appl. No. 14/242,177; Jan. 15, 2016; USPTO; Alexandria, Virgina; All Pages.
Apparatus and Method for Fusing Opposing Spinal Vertebrae, Bramlet, Dale G. et al., U.S. Appl. No. 09/635,436, filed Aug. 11, 2000,
Intervertebral nucleus prosthesis and surgical procedure for implanting the same, Gau, Michel, U.S. Appl. No. 10/060,862, filed Jan. 30, 2002.
Intersomatic cage with unified grafts, Huppert, Jean, U.S. Appl. No. 10/276,712, filed Mar. 26, 2003.
Spinal Osteosynthesis Device and Preparation Method, Beaurain, Jacques et al., U.S. Appl. No. 10/473,999, filed Apr. 12, 2004.
Intervertebral Disc Prosthesis and Fitting Tools, Beaurain, Jacques et al., U.S. Appl. No. 10/476,565, filed Jun. 8, 2004.
Vertebral Cage Device With Modular Fixation, Louis, Christian et al., U.S. Appl. No. 10/483,563, filed May 21, 2004.
Progressive approach osteosynthesis device and preassembly method, Delecrin, Joel et al., U.S. Appl. No. 10/492,753, filed Aug. 9, 2004.
Plate for osteosynthesis device and method of preassembling such device, Delecrin, Joel et al., U.S. Appl. No. 10/492,827, filed Jul. 15, 2004.
Osseous anchoring device for a prosthesis, Huppert, Jean et al., U.S. Appl. No. 10/494,418, filed Jul. 22, 2004.
Implant for Osseous Anchoring with Polyaxial Head, Beaurain, Jacques et al., U.S. Appl. No. 10/498,234, filed Dec. 7, 2004.
Intervertebral Disk Prosthesis, Beaurain, Jacques et al., U.S. Appl. No. 10/533,846, filed Nov. 11, 2005.
Osseous anchoring implant with a polyaxial head and method for installing the implant, Renaud, Christian et al., U.S. Appl. No. 10/570,080, filed Jun. 9, 2006.
Device and method for sectioning a vertebral lamina, Mangione, Paolo, U.S. Appl. No. 10/575,065, filed May 30, 2006.
Intervertebral Disc Prosthesis, Hovorka, Istvan et al., U.S. Appl. No. 11/051,710, filed Feb. 4, 2005.
Intervertebral Disc Prosthesis, Zeegers, M. Willem, U.S. Appl. No. 11/098,266, filed Apr. 4, 2005.
U.S. Appl. No. Intervertebral Disc Prosthesis, Zeegers, M. Willem, U.S. Appl. No. 11/109,276, filed Apr. 18, 2005.
Instrumentation and Methods for Inserting an Intervertebral Disc Prosthesis, Dinville, Herve, U.S. Appl. No. 11/180,868, filed Jul. 13, 2005.
Intervertebral Disc Prosthesis, Rashbaum, Ralph et al., U.S. Appl. No. 11/341,007, filed Jan. 27, 2006.
Intervertebral Disc Prosthesis and Instrumentation for Insertion of the Prosthesis Between the Vertebrae, Rashbaum, Ralph et al., U.S. Appl. No. 11/362,253, filed Feb. 24, 2006.
Transforanimal intersomatic cage for an intervertebral fusion graft and an instrument for implanting the cage, Davis, Reginald James et al., U.S. Appl. No. 11/378,165, filed Mar. 17, 2006.
Intervertebral nucleus prosthesis and surgical procedure for implanting the same, Gau, Michel, U.S. Appl. No. 11/390,711, filed Mar. 27, 2006.
Intervertebral disc prosthesis insertion assemblies, Jodaitis, Alexandre et al., U.S. Appl. No. 11/676,237, filed Feb. 16, 2007.
Intersomatic cage with unified grafts, Huppert, Jean, U.S. Appl. No. 11/767,386, filed Jun. 22, 2007.
Modular intervertebral prosthesis, Vila, Thierry et al., U.S. Appl. No. 11/874,144, filed Oct. 17, 2007.
Vertebral Support Device, Cho, Paul et al., U.S. Appl. No. 11/958,285, Dec. 17, 2007.
Intervertebral disc prosthesis, surgical methods, and fitting tools, Beaurain, Jacques et al., U.S. Appl. No. 12/025,677, Feb. 4, 2008.
Intersomatic cage, intervertebral prosthesis, anchoring device and implantation instruments, Allain, Jerome et al., U.S. Appl. No. 12/134,884, filed Jun. 6, 2008.
Transverse spinal linking device and system, Cho, Paul, U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, M. Willem, U.S. Appl. No. 12/360,050, filed Jan. 26, 2009.
Intervertebral Disc Prosthesis, Zeegers, M. Willem, U.S. Appl. No. 12/391,086, Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Intervertebral disc prosthesis insertion assemblies, Jodaitis, Alexandre et al., U.S. Appl. No. 12/527,373, filed Mar. 19, 2010.
Intervertebral implant having extendable bone fixation members, Brett, Darrell C., U.S. Appl. No. 12/884,664, filed Sep. 17, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervé et al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., U.S. Appl. No. 13/454,927, filed Apr. 24, 2012.
Anchoring Device and System for an Intervertebral Implant, Intervertebral Implant and Implantation Instrument, Dinville, Hervé et al., U.S. Appl. No. 13/520,041, filed Nov. 26, 2012.

(56) References Cited

OTHER PUBLICATIONS

Anchoring Device and System for an Intervertebral Implant, Intervertebral Implant and Implantation Instrument, Dinville, Hervé et al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, M. Willem, U.S. Appl. No. 13/603,043, filed Sep. 4, 2012.
Intervertebral Disk Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervé et al., U.S. Appl. No. 13/774,547, filed Feb. 22, 2013.
Transforanimal intersomatic cage for an intervertebral fusion graft and an instrument for implanting the cage, Davis, Reginald James et al., U.S. Appl. No. 13/854808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Prosthesis for Spinal Treatment, Jodaitis, Alexandre et al., U.S. Appl. No. 13/919,704, filed Jun. 17, 2013.
Intervertebral implant having extendable bone fixation members, Brett, Darrell C., U.S. Appl. No. 14/064,434, filed Oct. 28, 2013.
Interspinous Implant and Implantation Instrument, Dinville, Hervé et al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prostheses, Vila, Thierry et al., U.S. Appl. No. 14/159,161, filed Jan. 20, 2014.
Intervertebral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervé et al., U.S. Appl. No. 14/246,442, filed Apr. 7, 2014.
Interspinous Implant and Implantation Instrument, Dinville, Hervé et al., U.S. Appl. No. 14/252,754, filed Apr. 14, 2014.
Anchoring device for a spinal implant, spinal implant and implantation instrumentation, Chataigner, Hervé et al., U.S. Appl. No. 14/252,852, filed Apr. 15, 2014.
Intervertebral Disk Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Steib, Jean-Paul, U.S. Appl. No. 14/325,317, filed Jul. 7, 2014.
Anchoring device and system for an intervertebral implant, intervertebral implant and implantation instrument, Chataigner, Hervé et al., U.S. Appl. No. 14/380,714, filed Aug. 23, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis Hovorka, Istvan et al., U.S. Appl. No. 14/513,818, filed Oct. 14, 2014.
Plate for osteosynthesis device and method of preassembling such device, Delecrin, Joel et al., U.S. Appl. No. 14/584,674, filed Dec. 29, 2014.
Systems to Implant and Secure, Brett, Darrell C., U.S. Appl. No. 14/594,770, filed Jan. 12, 2015.
Vertebral implant, device for vertebral attachment of the implant and instrumentation for implantation thereof, Ameil, Marc et al., U.S. Appl. No. 14/638,746, filed Mar. 4, 2015.
Intervertebral Disc Prosthesis, Zeegers, M. Willem, U.S. Appl. No. 14/642,696, filed Mar. 9, 2015.
Vertebral Support Device, Cho, Paul et al., U.S. Appl. No. 14/642,752, filed Mar. 10, 2015.
Intervertebral Disc Prosthesis, Rashbaum, Ralph et al., U.S. Appl. No. 14/659,587, filed Mar. 16, 2015.
Anchoring device and system for an intervertebral implant, intervertebral implant and implantation instrument, Chataigner, Hervé et al., U.S. Appl. No. 14/721,818, filed May 26, 2015.
Intervertebral Disc Prosthesis, Zeegers, M. Willem, U.S. Appl. No. 14/726,557, filed May 31, 2015.
Anchoring Device and System for an Intervertebral Implant Intervertebral Implant and Implantation Instrument, Dinville, Hervé et al., U.S. Appl. No. 14/726,558, filed May 31, 2015.
Vertebral Cage Device With Modular Fixation, Louis, Christian et al., U.S. Appl. No. 14/798,900, filed Jul. 14, 2015.
Bone Implants, Lavigne, Christophe et al., U.S. Appl. No. 14/815,900, filed Jul. 31, 2015.
Devices, Methods, and Systems to Implant and Secure a Fusion Cage or Intervertebral Prosthesis for Spinal Treatment, Stewart, Will et al., U.S. Appl. No. 14/827,297, filed Aug. 15, 2015.
Vertebral implant, vertebral fastening device of the implant and implant instrumentation, Dinville, Herve et al., U.S. Appl. No. 14/891,322, filed Nov. 13, 2015.
Instruments and Methods for Removing Fixation Devices from Intervertebral Implants, Dinville, Herve et al., U.S. Appl. No. 14/931,007, filed Nov. 3, 2015.
U.S. Patent & Trademark Office; Office Action in U.S. Appl. No. 13/732,244; Oct. 20, 2015; USPTO; Alexandria, Virgina; All Pages.
LDR Medical, by its attorneys; Reply to Office Action in U.S. Appl. No. 13/732,244; Aug. 20, 2015; USPTO; Alexandria, Virgina; All Pages.
U.S. Patent & Trademark Office; Office Action in U.S. Appl. No. 13/732,244; Feb. 20, 2015; USPTO; Alexandria, Virgina; All Pages.
LDR Medical, by its attorneys; Reply to Office Action in U.S. Appl. No. 13/732,244; Jan. 20, 2015; USPTO; Alexandria, Virgina; All Pages.
U.S. Patent & Trademark Office; Notice of Allowance in U.S. Appl. No. 13/603,043; Feb. 10, 2015; USPTO; Alexandria, Virgina; All Pages.
LDR Medical, by its attorneys; Reply to Office Action in U.S. Appl. No. 13/603,043; Dec. 24, 2014; USPTO; Alexandria, Virgina; All Pages.
U.S. Patent & Trademark Office; Office Action in U.S. Appl. No. 13/603,043; Jul. 24, 2014; USPTO; Alexandria, Virgina; All Pages.
LDR Medical, by its attorneys; Reply to Office Action in U.S. Appl. No. 13/603,043; May 21, 2014; USPTO; Alexandria, Virgina; All Pages.
U.S. Patent & Trademark Office; Office Action in U.S. Appl. No. 13/585,063; Nov. 4, 2015; USPTO; Alexandria, Virgina; All Pages.
LDR Medical, by its attorneys; Reply to Office Action in U.S. Appl. No. 14/306,785; Sep. 22, 2015; USPTO; Alexandria, Virgina; All Pages.
LDR Medical, by its attorneys; Reply to Office Action in U.S. Appl. No. 13/585,063; Aug. 11, 2015; USPTO; Alexandria, Virgina; All Pages.
U.S. Patent & Trademark Office; Office Action in U.S. Appl. No. 13/585,063; Feb. 11, 2015; USPTO; Alexandria, Virgina; All Pages.
LDR Medical, by its attorneys; Reply to Office Action in U.S. Appl. No. 13/585,063; Jan. 6, 2015; USPTO; Alexandria, Virgina; All Pages.
U.S. Patent & Trademark Office; Office Action in U.S. Appl. No. 13/585,063; Nov. 6, 2014; USPTO; Alexandria, Virgina; All Pages.
U.S. Patent & Trademark Office; Notice of Allowance in U.S. Appl. No. 14/306,785; Oct. 13, 2015; USPTO; Alexandria, Virgina; All Pages.
U.S. Patent & Trademark Office; Office Action in U.S. Appl. No. 14/306,785; Jun. 22, 2015; USPTO; Alexandria, Virgina; All Pages.
LDR Medical, by its attorneys; Reply to Office Action in U.S. Appl. No. 14/306,785; Apr. 22, 2015; USPTO; Alexandria, Virgina; All Pages.
U.S. Patent & Trademark Office; Office Action in U.S. Appl. No. 14/306,785; Oct. 22, 2014; USPTO; Alexandria, Virgina; All Pages.

(56) References Cited

OTHER PUBLICATIONS

European Patent Office; search report in Application No. 13170071, Pub. No. EP2633835; Oct. 1, 2013; European Patent Office; Munich, Germany; All Pages.
European Patent Office; search report in Application No. 10185004, Pub. No. EP2327375; Apr. 6, 2011; European Patent Office; Munich, Germany; All Pages.
U.S. Patent & Trademark Office; Notice of Allowance in U.S. Appl. No. 13/438,352; Mar. 2, 2015; USPTO; Alexandria, Virgina; All Pages.
LDR Medical, by its attorneys; Reply to Office Action in U.S. Appl. No. 13/438,352; Jan. 14, 2015; USPTO; Alexandria, Virgina; All Pages.
LDR Medical, by its attorneys; Reply to Office Action in U.S. Appl. No. 14/721,818; Dec. 28, 2015; USPTO; Alexandria, Virgina; All Pages.
LDR Medical, by its attorneys; Notice of Allowance in U.S. Appl. No. 13/520,041; Nov. 18, 2015; USPTO; Alexandria, Virgina; All Pages.
U.S. Patent & Trademark Office; Notice of Allowance in U.S. Appl. No. 13/158,761; Sep. 25, 2015; USPTO; Alexandria, Virgina; All Pages.
U.S. Patent & Trademark Office; Office Action in U.S. Appl. No. 14/721,818; Sep. 24, 2015; USPTO; Alexandria, Virgina; All Pages.
U.S. Patent & Trademark Office; Notice of Allowance in U.S. Appl. No. 13/158,761; Sep. 2, 2015; USPTO; Alexandria, Virgina; All Pages.
LDR Medical, by its attorneys; Reply to Office Action in U.S. Appl. No. 13/520,041; Aug. 10, 2015; USPTO; Alexandria, Virgina; All Pages.
World Intellectual Property Organization; International Search Report and Written Opinion of the International Searching Authority for International App. No. WO2015114122, PCT Pub'n No. PCT/EP2015/052019; May 13, 2015; WIPO; Geneva, Switzerland; all pages.
U.S. Patent & Trademark Office; Notice of Allowance in U.S. Appl. No. 13/158,761; May 12, 2015; USPTO; Alexandria, Virgina; All Pages.
LDR Medical, by its attorneys; Reply to Office Action in U.S. Appl. No. 13/158,761; Apr. 22, 2015; USPTO; Alexandria, Virgina; All Pages.
U.S. Patent & Trademark Office; Office Action in U.S. Appl. No. 13/520,041; Apr. 10, 2015; USPTO; Alexandria, Virgina; All Pages.
LDR Medical, by its attorneys; Reply to Office Action in U.S. Appl. No. 13/520,041; Mar. 6, 2015; USPTO; Alexandria, Virgina; All Pages.
LDR Medical, by its attorneys; Reply to Office Action in U.S. Appl. No. 13/774,547; Feb. 2, 2015; USPTO; Alexandria, Virgina; All Pages.
U.S. Patent & Trademark Office; Notice of Allowance in U.S. Appl. No. 13/774,547; Feb. 2, 2015; USPTO; Alexandria, Virgina; All Pages.
U.S. Patent & Trademark Office; Office Action in U.S. Appl. No. 13/158,761; Oct. 22, 2014; USPTO; Alexandria, Virgina; All Pages.
U.S. Patent & Trademark Office; Notice of Allowance in U.S. Appl. No. 13/538,078; Oct. 20, 2014; USPTO; Alexandria, Virgina; All Pages.
U.S. Patent & Trademark Office; Notice of Allowance in U.S. Appl. No. 13/774,547; Oct. 16, 2014; USPTO; Alexandria, Virgina; All Pages.
LDR Medical, by its attorneys; Reply to Office Action in U.S. Appl. No. 13/538,078; Oct. 14, 2014; USPTO; Alexandria, Virgina; All Pages.
National Institute of Industrial Property (France); Search Report in Fench Pub. No. FR3016793, App. No. FR1450749; Sep. 11, 2014; National Institute of Industrial Property (France); France; all pages.
World Intellectual Property Organization; International Search Report for International App. No. WO2014184367, PCT Pub'n No. PCT/EP2014/060135; Aug. 26, 2014; WIPO; Geneva, Switzerland; all pages.
National Institute of Industrial Property (France); Search Report in Fench Pub. No. FR3005569, App. No. FR1354421; Feb. 12, 2014; National Institute of Industrial Property (France); France; all pages.
LDR Medical, by its attorneys; Amendment for Pub'n No. EP2519194, Application No. EP20090812464; May 23, 2013; EPO; Munich, Germany; all pages.

\* cited by examiner

INTERVERTEBRAL DISC PROSTHESIS

CROSS REFERENCE TO RELATED APPLICATIONS

This application is a continuation of U.S. application Ser. No. 12/955,898 filed Nov. 29, 2010, and issuing as U.S. Pat. No. 8,989,932 on Mar. 17, 2015, which is a continuation of U.S. application Ser. No. 11/341,007 filed Jan. 27, 2006, and issuing as U.S. Pat. No. 7,842,008 on Nov. 30, 2010, which claims priority from Application No. FR 0509740 filed in France on Sep. 23, 2005, all of which are incorporated herein by reference.

BACKGROUND

The invention relates to an intervertebral disc prosthesis, intended to be substituted for fibrocartilaginous discs providing the liaison between the vertebrae of the spinal column.

Different types of intervertebral disc prostheses are known in the prior art. Numerous prostheses, such as for example those described in the applications WO 02 089 701 and WO 2004/041129, are constituted of a lower plate and an upper plate creating a cage articulated about a central core. Other prostheses like those disclosed in the U.S. Pat. No. 5,676,701 and in the application WO 03/059212 A1, for example, only comprise a lower plate and an upper plate articulated about themselves by means of a surface of articulation. These articulated prostheses have the advantage of offering the patient bearing the prosthesis a freedom of movement, by allowing the plates to tilt and/or rotate in relation to each other. The prostheses comprising a central core, movable between the plates, have the added advantage of allowing a spontaneous positioning of the core in the ideal position for absorbing the constraints imposed on the prosthesis. In these prostheses known in the prior art, the anterior, posterior and lateral edges of a plate are located on the same vertical axis as the corresponding edge of the other plate. This shape of the prosthesis is normally due to the plates being of identical size and that their respective axes of articulation are joined (coaxially), so as to facilitate the movements of the patient and to allow the correction of possible positioning defects. However, these prostheses have the inconvenience of not being perfectly suited to the morphology of the spinal column. Indeed, the posterior edges of two adjacent vertebrae are often slightly off-set to each other. Thus, the prostheses known in the prior art are difficult to properly implant. Additionally, at rest, due to the natural off-setting of the vertebrae and the anchoring of the plates in the vertebrae, the different parts of the prosthesis are under constraint in an undesirable position as it restricts freedom of movement of these parts of the prosthesis. This inconvenience will be diminished through the use of a movable core between the plates, but the possible movements of the core will be restricted and its capacity to position itself so as to absorb the constraints imposed on the prosthesis will therefore be diminished.

In this context, it is beneficial to propose a prosthesis that allows a more efficiently fit to the profile of the spinal column and thus fully attain the goals it set by offering a surface of articulation.

SUMMARY

The purpose of the invention is to overcome some of the inconveniences of the prior art by proposing an intervertebral disc prosthesis at least comprising two plates each bearing at least an edge off-set in relation to the same edge of the other plate.

This goal is reached with an intervertebral disc prosthesis comprising at least two plates, namely first and second plates, articulated about each other by means of a curved surface, namely articulation, of at least one of the plates, allowing to pivot and/or tilt the plates in relation to each other, via rotation about, respectively, an axis substantially perpendicular to the plane of the plates and an axis substantially in the plane of the plates, each of the plates comprising a surface known as a contact surface, intended to be in contact with a vertebral plate of one of the vertebrae between which the prosthesis is intended to be implanted, this contact surface for each of the plates comprising a geometric centre at equal distance from at least two diametrically opposite points located on the periphery of the plate, characterised in that the geometric centres of the plates are not vertically aligned, this off-set of the geometrical centres of the plates engendering an off-set of the edges of the plates in at least one direction perpendicular to the vertical axis of the spinal column.

According to another feature, the second plate comprises a curved surface of articulation of which at least one part co-operates with a curved surface of articulation of the first plate for which it is complementary, in order to allow the articulation, by pivoting and/or tilting, of the plates in relation to each other, the prosthesis comprising a centre of articulation vertically aligned with the vertex of the curved surface of articulation of the second plate and corresponding to the mid-position of the centre of the curved surface of the first plate in relation to the second plate.

According to another feature, the curved surface of the first plate is concave and the curved surface of articulation of the second plate is convex.

According to another feature, the curved surface of the first plate is convex and the curved surface of articulation of the second plate is concave.

According to another feature, the prosthesis also comprises a core comprising a plane surface and a curved surface of articulation and in that only the first plate comprises a curved surface of articulation co-operating with at least one part of the curved surface of the core for which it is complementary, in order to allow the pivoting and/or tilting of the plates in relation to each other, the plane surface of the core co-operating with at least one part of a plane surface of the second plate in order to allow a translation and/or a rotation of the core in relation to the second plate in at least one direction perpendicular to the vertical axis of the spinal column, the second plate comprising means for co-operating complementary with means for co-operating of the core allowing to restrict or abolish at least this translation of the core in relation to the second plate, the prosthesis comprising a centre of articulation vertically aligned with the vertex of the curved surface of articulation of the core and corresponding to the mid-position of the core between the means for co-operating of the second plate and to the mid-position of the centre of the curved surface of the first plate in relation to the core.

According to another feature, the curved surface of the first plate is concave and the curved surface of the core is convex.

According to another feature, the curved surface of the first plate is convex and the curved surface of the core is concave.

According to another feature, the prostheses comprises a centre of articulation vertically aligned with the vertex of the curved surface of articulation, said centre of articulation being vertically aligned with the geometric centre of the first plate but off-set in relation to the geometric centre of the second plate in at least one direction perpendicular to the vertical axis of the spinal column, this off-setting of the geometric centres of the plates engendering an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate but in the opposite direction to that of its off-setting in relation to the geometric centre of the second plate, so that the vertical projection of the centre of articulation is located between the vertical projections of the geometric centres of the plates and that the off-setting of the geometric centres in relation to the centre of articulation cumulate and engender an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate, in the same direction as that of its off-setting in relation to the geometric centre of the second plate, but at a lesser distance so that these off-settings partially compensate each other and engender an off-setting of the edges of the plates between themselves in at least one direction perpendicular to the vertical axis of the spinal column.

According to another feature, the means for co-operating of the second plate are female means located in the vicinity of the edges of the second plate and co-operating with the male means of the core.

According to another feature, the dimensions of each male means for co-operating are slightly smaller than those of the female means for co-operating in order to allow a slight travel between the core and the second plate around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the means for co-operating of the second plate are the male means located in the vicinity of the edges of the second plate and co-operating with the female means of the core.

According to another feature, the dimensions of each male means for co-operating are slightly smaller than those of each female means for co-operating in order to allow as slight travel between the core and the second plate, around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the male means for co-operating of the core are two studs located on the two side edges of the core and the female means for co-operating of the second plate are four walls located, in pairs, on each of the two side edges of the second plate.

According to another feature, the female means for co-operating of the second plate comprise a section dish-shaped towards the centre of the plate and partly covering the male means for co-operating of the core in order to prevent the core from lifting.

According to another feature, the median planes representing the contact surfaces of the plates are substantially parallel or create an acute angle, the slope obtained by such an angle allowing to adapt the overall shape of the prosthesis to the anatomy of the spinal column or to possibly correct any slope defects of the vertebrae of the patient for whom the prosthesis is intended for.

According to another feature, the plates comprise, at least on their lower edge, at least a bevel facilitating the insertion of the prosthesis between the vertebrae.

According to another feature, the same plates can be assembled with cores of different thicknesses and/or dimensions and/or shapes.

According to another feature, the plates comprise mobile osseous anchorage means.

According to another feature, the osseous anchorage means and/or the plates comprise means for securing the binding of the osseous anchorage means on the plates.

According to another feature, the mobile osseous anchorage means of the plates consists in at least one plate equipped with notches oriented so as to prevent this notched plate from falling out once inserted in a vertebra, one end of the plate having an inward curving section and intended to be interlocked onto at least one edge of an opening located in the vicinity of the periphery of the plates.

According to another feature, the end of the notched plate, opposite the one with an inward curving section, comprises a bevel facilitating the insertion of the notched plate into the vertebrae.

According to another feature, the opening located in the vicinity of the periphery of the plates comprises a sloping section on which the notched plate leans when the curved section of the osseous anchorage means is interlocked onto the edge of this opening, this sloping section thus allowing to set the angle of the osseous anchorage means in relation to the plates and to guide them when being inserted into the opening.

According to another feature, the means for securing consist in flexible tabs oriented towards the curved section of the osseous anchorage means and intended to fold back against the edges of the plate when inserting the osseous anchorage means into the openings in the plates, then to spring back so as to lean against the limit stops located on the walls of the openings in the plates during the interlocking of the curved sections onto the edges of the openings in the plates, so as to prevent the osseous anchorage means from falling out.

According to another feature, the inward curving section of the notched plate of the mobile osseous anchorage means extends by means of a second plate also equipped with notches oriented so as to prevent the plate from falling out once inserted into the vertebra.

According to another feature, the mobile osseous anchorage means of the plates consist in at least a winglet equipped with notches oriented so as to prevent the winglet from falling out once inserted in a groove made in a vertebra, one end of the winglet having an inward curving section and intended to be interlocked on to at least one edge of an opening in the vicinity of the periphery of the plates.

According to another feature, the means for securing the winglet consist in at least one stud located on the lower surface of the winglet and intended to be interlocked into at least one hole in the contact surfaces of the plates, the stud and the hole being of complementary shape and size so as to secure the winglet in place on the plates.

BRIEF DESCRIPTION OF THE DRAWINGS

Other features and advantages of the invention will become clearer upon reading the following description, given in reference to the annexed figures, in which.

DETAILED DESCRIPTION OF THE EMBODIMENTS

Figure 1A:
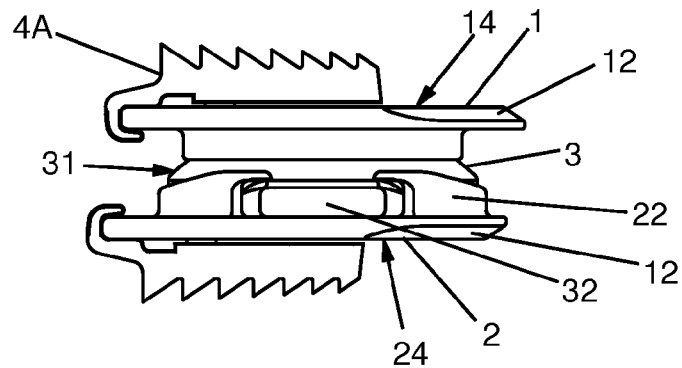
FIGS. 1A, 1B and 1C respectively represent a side view, a rear view with a cross section plane 1C-1C and a cross section along said plane 1C-1C, of an intervertebral disc prosthesis according to an embodiment of the invention, FIGS. 2A, 2B and 2C respectively represent a side view, a rear view with a cross section plane 2C-2C and a cross section along said plane 2C-2C, of an intervertebral disc prosthesis according to another embodiment of the invention, FIGS. 3A and 3B respectively represent a rear view with a cross section plane 3B-3B and a cross section along said plane 3B-3B, of an intervertebral disc prosthesis according to an embodiment of the invention and FIGS. 3C and 3D respectively represent a rear view with a cross section plane 3D-3D and a cross section along said plane 3D-3D, of an intervertebral disc prosthesis according to another embodiment of the invention, FIGS. 4A and 4B respectively represent a top view and a perspective view of an embodiment of the osseous anchorage means of an intervertebral disc prosthesis according to the invention, and FIGS. 4C and 4D respectively represent a top view and a side view of another embodiment of the osseous anchorage means of an intervertebral disc prosthesis according to the invention, FIGS. 5A, 5B and 5C respectively represent a perspective view, a top view and a side view of an intervertebral disc prosthesis according to different embodiments of the invention.

The invention relates to an intervertebral disc prosthesis comprising at least two plates (1, 2) off-set in relation to each other so as to more efficiently follow the anatomy of the spinal column. As explained in the preamble of this application, the vertebrae are generally slightly off-set to each other, so that their edges, for example posterior, are not vertically aligned. The prosthesis according to the invention is thus designed so that the edges of the plates (1, 2) are not vertically aligned and have a slight off-setting corresponding to an off-setting between the edges of the vertebrae between which the prosthesis is intended to be inserted. The off-setting of the vertebrae could have been accurately measured beforehand, in order to choose a prosthesis whose off-setting of the plates (1, 2) perfectly corresponds to the off-setting of the vertebrae.

The plates (1 and 2) of the prosthesis according to the invention each comprise a geometric centre (G1 and G2, respectively) which can be defined, generally speaking, by a point at equal distance from two diametrically opposite points located on the periphery of the plates (1, 2). Normally, the plates of the intervertebral disc prostheses have a relatively straightforward shape and their geometric centre can be of equal distance from all the points located on the periphery of the plates. Irrespective of the prosthesis, a geometric centre can be defined by a point or a surface located at equal distance from the edges of the plate. The geometric centres (G1, G2) of the plates (1, 2) of the prosthesis according to the invention are not vertically aligned but are off-set to each other in at least one direction, for example antero-posterior, perpendicular to the vertical axis of the spinal column. The two plates (1 and 2) of a single intervertebral disc prosthesis are usually substantially the same size and this off-set (D) of the geometric centres (G1, G2) of the plates engenders an off-set of the edges of the plates (1, 2). In the case of a prosthesis whose plates are not of the same size, it is envisaged to off-set the edges of the plates (1 and 2) and the geometric centres (G1, G2) will be even more off-set to each other.

In the different embodiments described below, the prosthesis comprises at least two plates (1 and 2), namely first (1) and second (2) plates, articulated about each other by means of a curved surface (11, 31), namely articulation, of at least one of the plates. This curved surface (11, 31) of articulation allows to pivot the plates (1, 2) about each other, via rotation about an axis substantially perpendicular to the plane of the plates and/or to tilt the plates (1, 2) about each other, via rotation about an axis substantially along the plane of the plates (1, 2). Each of the plates (1, 2) comprises a surface (14, 24) known as a contact surface, intended to be in contact with a vertebral plate of one of the vertebrae between which the prosthesis is intended to be inserted. The geometric centre will hereafter be defined in relation to this contact surface for the sake of ease but it must be understood that it is the vertical axis passing through the geometric centre which matters in the principle of the invention and that the exact position of the geometric centre on the width of the plates has no relevance. In the different embodiments described below, each of the plates (1, 2) therefore comprises a geometric centre (G1, G2) at equal distance from at least two diametrically opposite points located on the periphery of the plate (1, 2). The geometric centres (G1, G2) of the plates (1, 2) are not vertically aligned and this off-set (D) of the geometrical centres (G1, G2) of the plates engenders an off-set of the edges of the plates (1, 2) in at least one direction perpendicular to the vertical axis of the spinal column.

Figure 2A:
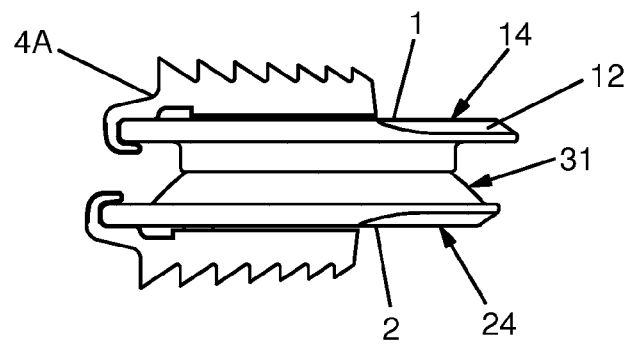
Figure 2B:
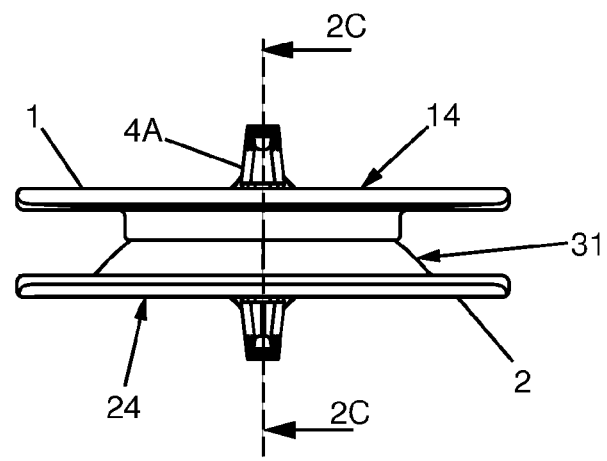
Figure 2C:
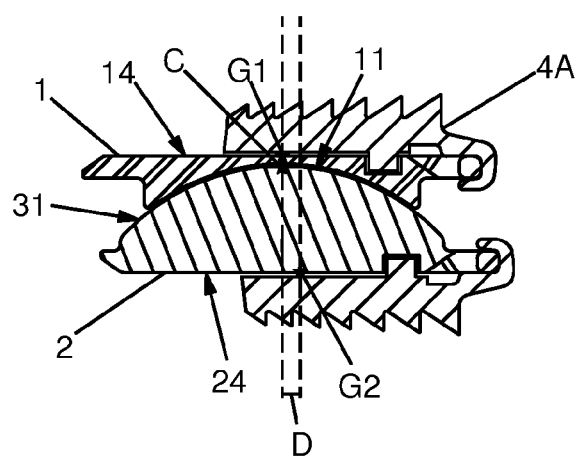
Figure 3A:
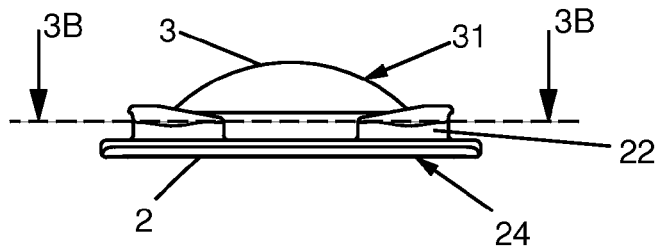
Figure 3B:
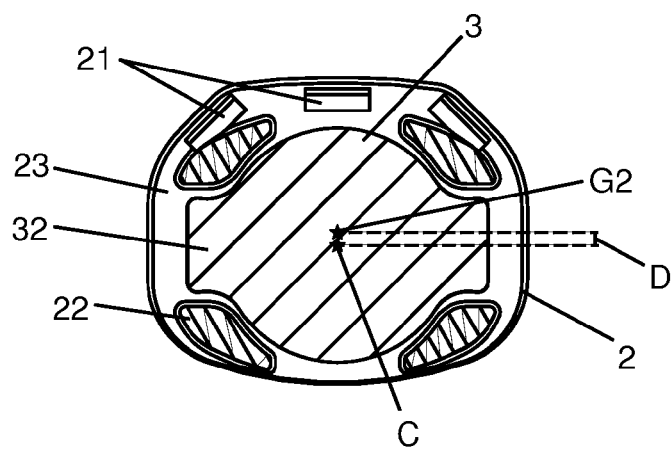
Figure 3C:
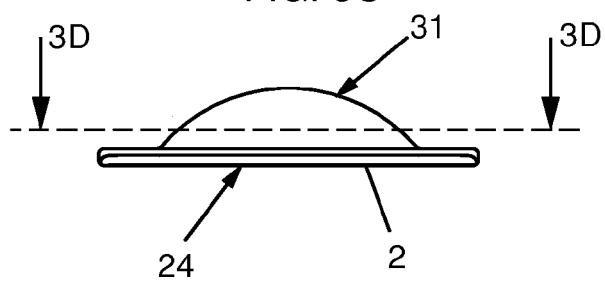
Figure 3D:
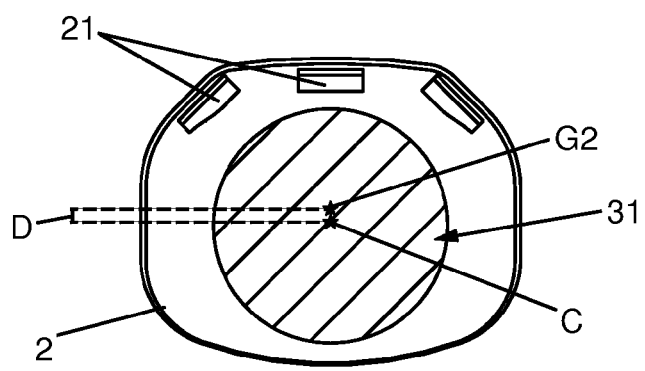
Figure 4A:
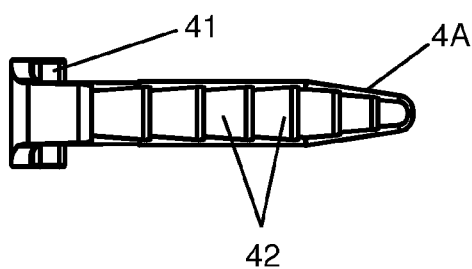
Figure 4B:
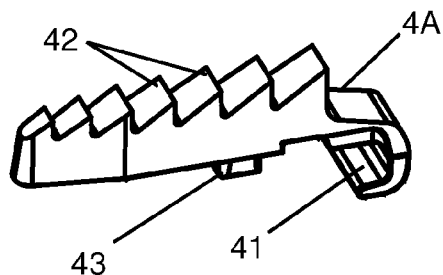
Figure 4C:
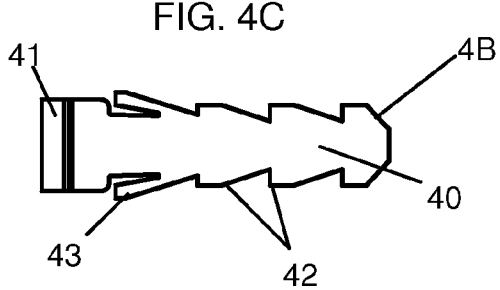
Figure 4D:
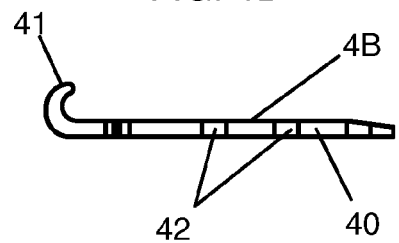

In the embodiment represented in FIGS. 2A, 2B, 2C, 3C and 3D, the prosthesis only comprises two elements: two plates (1, 2). In this case, the second plate (2) comprises a curved surface (31) of articulation of which at least one section co-operates with a curved surface (11) of articulation of the first plate (1) to which it is complementary. The co-operating of these curved surfaces (11, 31) of articulation allows to pivot and/or tilt the plates (1, 2) about each other. A centre (C) of articulation vertically aligned with the vertex of the curved surface (31) of articulation of the second plate (2) can be defined. This centre (C) of articulation corresponds to the mid-position of the centre of the curved surface (11) of the first plate (1) compared to the second plate (2). In the embodiment represented in the figures, the curved surface (11) of the first plate (1) is concave and the curved surface (31) of articulation of the second plate (2) is convex but it can be the case that the curved surface (11) of the first plate (1) is convex and that the curved surface (31) of articulation of the second plate (2) is concave.

Figure 1B:
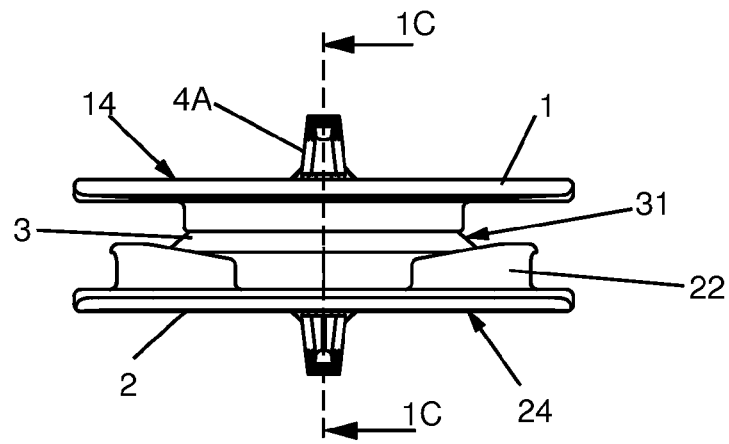
Figure 1C:
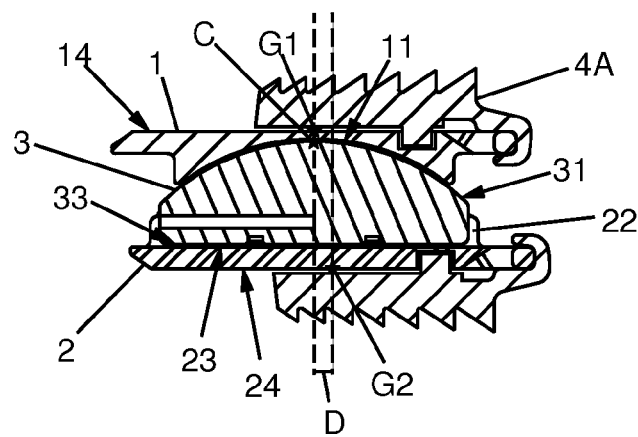
Figure 5A:
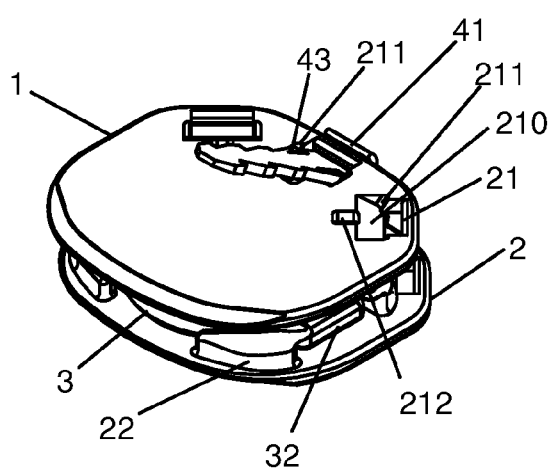
Figure 5B:
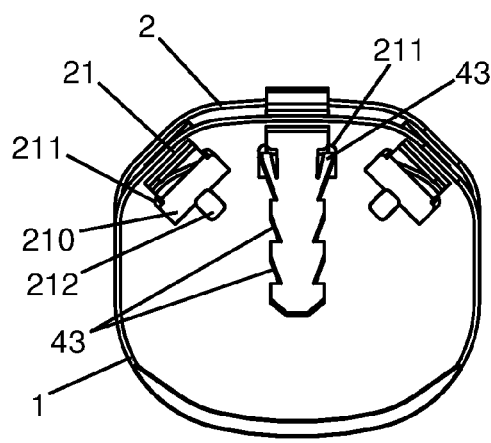
Figure 5C:
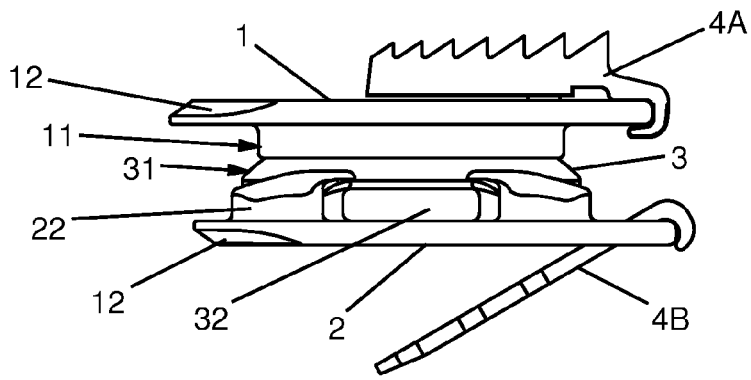

In the embodiment represented in FIGS. 1A to 1C, 3A, 3B and 5A to 5C, the prosthesis also comprises a core (3) comprising a plane surface (33) and a curved surface (31) of articulation. In the case of a prosthesis with three elements, only the first plate (1) comprises a curved surface of articulation (11) and this surface co-operates with at least a section of the curved surface (31) of the core (3) to which it is complementary, to allow to pivot and/or tilt the plates (1, 2) about each other. The plane surface (33) of the core (3) co-operates with at least a section of a plane surface (23) of the second plate (2) to allow a translation of the core (3) in relation to the second plate (2) in at least one direction perpendicular to the vertical axis of the spinal column and/or a rotation of the core (3) in relation to the second plate (2) via rotation about an axis substantially perpendicular to the plane of these plane surfaces. The second plate (2) comprises means for co-operating (22) which are complementary with means for co-operating (32) of the core (3) so as to restrict or abolish at least this translation of the core (3) in relation to the second plate (2). In the embodiments represented in figures, the means for co-operating (22) of the second plate (2) are female means located in the vicinity of the edges of the second plate (2) and co-operating with the male means (32) of the core (3). In the embodiments represented in the figures, these male means for co-operating (32) of the core (3) are two studs located on the two side edges of the core (3) and the female means for co-operating (22) of the second plate (2) are four walls located, in pairs, on each of the two side edges of the second plate (2). These walls comprise an inward curving section towards the centre of the plate (2) and partially covering the male means for co-operating (32) of the core (3) so as to prevent the core (3) from lifting. In another embodiment of the invention, the means for co-operating (22) of the second plate (2) can be male means located in the vicinity of the edges of the second plate (2) and co-operating with the female means (32) of the core (3). In an embodiment of the invention, the dimensions of each male means for co-operating (32, 22) can be slightly smaller than those of the female means for co-operating (22, 32) so as to allow a slight travel between the core (3) and the second plate (2) around the position corresponding to the vertical projection of the centre (C) of articulation. In another embodiment, the dimensions of each male means for co-operating (32, 22) can be substantially identical to those of each female means for co-operating (22, 32) so as to prevent any travel between the core (3) and the second plate (2) and to retain the core (3) in the position corresponding to the vertical projection of the centre (C) of articulation.

In this case of a prosthesis with three elements, the centre (C) of articulation is vertically aligned with the vertex of the curved surface (31) of articulation of the core (3) and correspond to the mid-position of the core (3) between the means for co-operating (22) of the second plate (2) and to the mid-position of the centre of the curved surface (11) of the first plate (1) in relation to the core (3). In the embodiment represented in the figures, the curved surface (11) of the first plate (1) is concave and the curved surface (31) of the core (3) is convex but it could be that the curved surface (11) of the first plate (1) is convex and that the curved surface (31) of the core (3) is concave.

In an embodiment of the invention, the centre (C) of articulation is vertically aligned with the centre (G1) of geometry of the first plate (1) but off-set in relation to the geometric centre (G2) of the second plate (2) in at least a direction perpendicular to the vertical axis of the spinal column. This off-setting (D) of the geometric centres (G1, G2) of the plates engenders an off-setting of the edges of the plates (1, 2) in at least one direction perpendicular to the vertical axis of the spinal column. In another embodiment of the invention, the centre (C) of articulation can also be off-set in relation to the geometric centre (G1) of the first plate (1). This off-setting of the centre (C) of articulation in relation to the geometric centre (G1) of the first plate (1) can be in the opposite direction to that of its off-setting (D) in relation to the geometric centre (G2) of the second plate (2) so that the vertical projection of the centre (C) of articulation lies between the vertical projections of the geometric centres (G1, G2) of the plates (1, 2) and so that the off-setting of the geometric centres (G1, G2) in relation to the centre (C) of articulation cumulate and engender an off-setting of the edges of the plates (1, 2) in at least one direction perpendicular to the vertical axis of the spinal column. This off-setting of the centre (C) of articulation in relation to the geometric centre (G1) of the first plate (1) can also be in the same direction as that of its off-setting (D) in relation to the geometric centre (G2) of the second plate (2), but at a lesser distance so that these off-settings partially compensate each other and engender an off-setting of the edges of the plates (1, 2) between themselves in at least one direction perpendicular to the vertical axis of the spinal column.

It can be beneficial that prostheses according to various embodiments of the invention allow correction of the slope defects of the adjacent vertebrae. The median planes representing the contact surfaces (14, 24) of the plates (1, 2) can therefore be substantially parallel or create an acute angle. The slope obtained by such an angle will allow the overall shape of the prosthesis to be adapted to the anatomy of the spinal column or to correct any possible slope defects of the vertebrae of the patient for whom the prosthesis is intended. The same plates (1, 2) are assembled with core (3) of different thicknesses and/or dimensions and/or shapes. The plates (1, 2) can comprise, at least on their anterior edge, at least a bevel (12) facilitating the insertion of the prosthesis between the vertebrae.

An embodiment of a prosthesis according to the invention comprises mobile osseous anchorage means (4A, 4B) allowing to anchor the plates (1, 2) in the vertebrae. These osseous anchorage means (4A, 4B) and/or the plates (1, 2) can thus comprise means for securing (43 and/or 211, 212) of the binding of the osseous anchorage means (4A, 4B) on the plates (1, 2).

In one embodiment of the mobile osseous anchorage means (4B), at least a plate (40), equipped with notches (42) oriented so as to prevent this notched plate (40) from falling out once inserted in a vertebra, is intended to be interlocked on to at least one edge (21) of an opening in the vicinity of the periphery of the plates (1, 2), thanks to an inwardly curved section (41). Thus, these mobile osseous anchorage means (4B) can be inserted into the vertebrae and interlocked on to the plates of the prosthesis once the latter has been inserted between the vertebrae. This embodiment of the mobile osseous anchorage means (4B) allows a possible adjustment of the position of the prosthesis between the vertebrae prior to definitive bonding. The end of the notched plate (40) opposite the one with an inwardly curved section (41) can comprise a bevel allowing to facilitate the insertion of the notched plate (40) into the vertebrae. The opening in the vicinity of the periphery of the plates (1, 2) can comprise a sloping section (210) on to which the notched plate (40) leans when the curved section (41) of the osseous anchorage means (4B) is interlocked on to the edge (21) of this opening. This sloping section (210) allows to set the angle of the osseous anchorage means (4B) in relation to the plates and to guide them when they are being inserted into the opening. The means for securing (43) can consist of flexible tabs (43) oriented towards the curved section (41) of the osseous anchorage means (4B) and intended to fold back against the edges of the plate (40) when inserting the osseous anchorage means (4B) into the openings in the plates (1, 2).

During the interlocking of the curved sections (41) onto the edges (21) of the openings in the plates (1, 2), these flexible tabs (43) separate to lean against the limit stops (211) located on the walls of the openings in the plates (1, 2), so as to prevent the osseous anchorage means (4B) from falling out. In an alternative embodiment, the inwardly curved section (41) of the notched plate (40) of the mobile osseous anchorage means (4B) extends via a second plate also equipped with notches (42) oriented so as to prevent the plate from falling out once inserted into the vertebrae.

In another embodiment the mobile osseous anchorage means (4A, 4B) of the plates (1, 2) includes at least one winglet (4A) equipped with notches (42) oriented so as to prevent the winglet (4A) from falling out once inserted into a groove made in a vertebra. One end of the winglet (4A) has an inwardly curved section (41) intended to be interlocked on to at least one edge (21) of an opening in the vicinity of the periphery of the plates (1, 2). The means for securing (43) of the winglet (4A) can thus comprise at least a stud (43) located on the lower surface of the winglet (4A) and intended to be interlocked into at least one hole (210) on the contact surfaces (14, 24) of the plates (1, 2). The stud (43) and the hole (210) will be of complementary shape and size so as to secure the winglet (4A) on to the plates (1, 2). In this embodiment, the vertebrae, between which the prosthesis is intended to be inserted, will have been previously prepared by the surgeon by hollowing out, in the vertebral plates, grooves of complementary shape and size with the shape and size of the winglets (4A).

It should be obvious for those skilled in the art that the invention allows embodiments under numerous other specific forms whilst remaining within the scope of the invention as claimed. Consequently, the embodiments should be considered as purely illustrative, but can be modified in the field defined by the impact of the attached claims, and the invention should not be restricted to the aforementioned details.

The invention claimed is:

1. An elongated intervertebral device anchor having a longitudinal axis and longitudinal sides, the anchor comprising:
    a device retaining end;
    a penetration end opposite the device retaining end along the longitudinal axis;
    a plate like body disposed between the retaining end and the penetrating end, the body having a rectangular cross section perpendicular to the longitudinal axis defining top and bottom surfaces that are wider than lateral side surfaces in the cross section, the plate like body comprising a curved section in which the top and bottom surfaces bend along the longitudinal axis, with the top surface being concave and the bottom surface being convex in said section;
    a first locking tab protruding from one of the lateral side surfaces disposed between the device retaining end and the penetration end; and
    teeth along at least a portion of each of the longitudinal sides of the anchor, the teeth configured to retain the anchor in a vertebra.

2. The anchor of claim 1 further comprising a second locking tab protruding from a lateral side surface opposite the lateral side surface from which the first locking tab protrudes.

3. The anchor of claim 2 in which the first and second locking tabs are resilient tangs.

4. The anchor of claim 3 in which the teeth have a leading edge oriented angularly to the longitudinal axis and extending away from the plate-like body toward the device retaining end.

5. The anchor of claim 4 in which the penetration end comprises a bevel formed by a narrowing of the distance between the top and bottom surfaces.

6. An intervertebral device anchor comprising a first elongated plate-like body having a length, a width defined by opposing lateral edges, and a thickness defined by a top surface and a bottom surface, with the length greater than the width and the width greater than the thickness, the anchor comprising:
    a curved portion in which the top is concave along the length and the bottom is convex along the length;
    a first end and a second end disposed at opposite ends of the length;
    a retainer disposed on each of the lateral edges between the first end and the second end; and
    an interlock disposed at the second end.

7. The anchor of claim 6 in which each of the retainers comprises a resilient tab extending from the first plate-like body and angled away from the first end.

8. The anchor of claim 7 in the curved portion comprises the interlock.

9. The anchor of claim 8 further comprising a second plate-like body disposed adjacent to the first plate-like body and joined to the first plate-like body by the curved portion.

10. An elongated anchor for an intervertebral device comprising:
    a first end disposed at a longitudinal extremity of the anchor;
    a second end disposed at an opposite longitudinal extremity of the anchor and comprising a retainer configured to hold the anchor in the device;
    a longitudinal axis extending from the first end to the second end and lying in a longitudinal plane dissecting the anchor into lateral halves;
    a first transverse axis extending perpendicularly to the longitudinal plane;
    a second transverse axis lying in the longitudinal plane and extending perpendicularly to the first transverse axis;
    a first plate-like body extending between the first end and the second end, the plate-like body comprising
        a top side and a bottom side disposed on opposite sides of the longitudinal axis along the second transverse axis, each of the top and bottom sides having a width extending perpendicularly to the longitudinal plane and a length extending in the longitudinal plane,
        lateral sides extending between the top and bottom sides, each of the lateral sides being disposed on an opposite side of the longitudinal axis along the first transverse axis and having profiles that are generally symmetrical about the longitudinal axis, and
        notches along the lateral sides of the plate-like body; and
    a locking tab protruding from the plate-like body between the first end and the second end proximal to the second end.

11. The anchor of claim 10 in which the longitudinal axis comprises a curved segment, with the top side of the plate-like body being convex proximal to the curved segment in the direction of the longitudinal axis and the bottom side of the plate-like body being concave proximal to the curved segment in the direction of the longitudinal axis.

12. The anchor of claim 11 in which the retainer is disposed along a lateral side of the plate-like body where the top side is convex and the bottom side is concave.

* * * * *